(12) United States Patent
Talbot et al.

(10) Patent No.: US 10,370,637 B2
(45) Date of Patent: Aug. 6, 2019

(54) TECHNOLOGY FOR SUSTAINING PLURIPOTENCY AND IMPROVED GROWTH OF STEM CELLS IN CULTURE

(71) Applicant: The Regents of the University of California, Oakland, CA (US)

(72) Inventors: Prudence Talbot, Riverside, CA (US); Sabrina Lin, Silverado, CA (US); Antonio Loza, Indio, CA (US)

(73) Assignee: The Regents of the University of California, Oakland, CA (US)

( * ) Notice: Subject to any disclaimer, the term of this patent is extended or adjusted under 35 U.S.C. 154(b) by 14 days.

(21) Appl. No.: 15/380,811

(22) Filed: Dec. 15, 2016

(65) Prior Publication Data

US 2017/0166861 A1 Jun. 15, 2017

Related U.S. Application Data

(60) Provisional application No. 62/267,840, filed on Dec. 15, 2015.

(51) Int. Cl.
*C12N 5/00* (2006.01)
*C12N 5/0735* (2010.01)

(52) U.S. Cl.
CPC ...... *C12N 5/0606* (2013.01); *C12N 2501/999* (2013.01)

(58) Field of Classification Search
CPC ................. C12N 5/0606; C12N 2501/999
See application file for complete search history.

(56) References Cited

U.S. PATENT DOCUMENTS

| 8,603,818 B1 * | 12/2013 | Hochedlinger | C12N 5/0696 |
| | | | 435/325 |
| 2012/0195969 A1 | 2/2012 | Riordan et al. | |
| 2015/0017135 A1 | 1/2015 | Agulnick | |

OTHER PUBLICATIONS

Wang et al. Stem Cell Research 17:273-276, 2016 (Year: 2016).*
Printout from https://pubchem.ncbi.nlm.nih.gov/compound/acetic_acid#section=Top, pp. 1 to 135, printed May 23, 2018 (Year: 2018).*
De Jong et al. Toxicological Sciences 110(1):117-124, 2009 (Year: 2009).*

* cited by examiner

*Primary Examiner* — Marcia S Noble
(74) *Attorney, Agent, or Firm* — Brooks Kushman P.C.

(57) ABSTRACT

A method of culturing pluripotent stem cells is provided. The method includes culturing pluripotent stem cells in a pluripotent stem cell culture medium supplemented with an additive, where the additive includes a source of acetate ions, a carboxylic acid, or a physiologically acceptable salt of the carboxylic acid, or a combination of these substances, in an amount effective to maintain the pluripotent stem cells in culture in an undifferentiated pluripotent state. Also included are pluripotent stem cell culture media and methods of making such media.

6 Claims, 6 Drawing Sheets

TECHNOLOGY FOR SUSTAINING PLURIPOTENCY AND IMPROVED GROWTH OF STEM CELLS IN CULTURE

CROSS-REFERENCE TO RELATED APPLICATIONS

This application claims the benefit of Provisional Patent Application No. 62/267,840, filed on Dec. 15, 2015, which is incorporated by reference herein

STATEMENT REGARDING FEDERALLY SPONSORED RESEARCH OR DEVELOPMENT

This invention was made with Government support under Grant No. DA036493 from the National Institutes of Health. The Government has certain rights in this invention.

BACKGROUND

Field of the Invention

The invention relates to cell culture media for maintaining pluripotent stem cells.

Related Art

Pluripotent stem cells (PSC) divide (self-renew) indefinitely in culture, and they have the ability to differentiate into any of the cells found in an adult. PSC have many important applications in biology and medicine. While culture media for PSC have improved over the last decade, there are still problems with existing media and improvements need to be made. A major problem with existing commercially available media is that they do not reliably hold the PSC in an undifferentiated, pluripotent state. Others have had the same problem; PSC do not maintain pluripotency well in commercial media. Not being able to maintain pluripotency is a serious problem. If this problem is not solved, performing rigorous experiments in research, translational and clinical labs will be hampered if not precluded.

SUMMARY

Described herein is an additive that can be added to culture media intended for use with pluripotent stem cells. Cell quality can be improved in the culture medium in five ways: (1) cells can attach to and spread faster on the substrate (faster attachment and spreading correlates with healthy colonies that do not differentiate); (2) cells do not differentiate even with repeated passaging; (3) fewer cells die in the supplemented medium; (4) cells can grow at a faster rate in medium with the supplement; and/or (5) colony/cell motility can be greater in the supplemented culture medium (this is important as it helps colonies form quickly which prevents cell death). Each of these factors provides tremendous advantages in colony morphology, growth, survival, maintenance of pluripotency, and dynamic behavior when compared to existing media. Maintenance of pluripotency is especially important. The additive enables the culture medium to maintain cells in a pluripotent state without evidence of differentiation. Cells in medium with the chemical additive express markers for pluripotency and when transferred to differentiation medium, cells express markers for differentiation. In some embodiments, the chemical additive is a non-toxic biological compound that is not harmful to cells. It would be suitable for use in media that are intended for clinical applications of stem cell technology and would not require special FDA approval for use with cells prepared for patients. These embodiments could be of tremendous benefit to labs working with pluripotent stem cells. This xeno-free and serum-free supplement stabilizes the culture medium so that pluripotency is enhanced and maintained. These embodiments would have application in all labs that work with PSC (this includes basic, translational, and clinical labs).

In one aspect, a method for improving the culturing of pluripotent stem cells in a pluripotent stem cell (PSC) culture medium is provided. The method includes: a) supplementing the PSC culture medium with an additive that includes a source of acetate ions, a metabolic derivative of acetic acid, a carboxylic acid, or a physiologically acceptable salt of the carboxylic acid, or a combination thereof; and b) culturing the pluripotent stem cells in the supplemented PSC culture medium. In the method, the additive is supplemented in an amount effective to maintain pluripotency of the pluripotent stem cells to a greater extent as compared to control pluripotent cells cultured in the PSC culture medium not supplemented with the additive. Thus, more cells in the supplemented medium maintain a pluripotent state compared to the controls cells in the non-supplemented medium. Pluripotency can be determined, for example, by the morphology and behavior of the pluripotent cells, or by the presence or absence of molecular biomarkers. For example, more cells in the supplemented medium express pluripotency markers, or less cells in the supplemented medium express differentiation markers, compared to the controls cells in the non-supplemented medium.

In some embodiments of the method: a) the pluripotency of the pluripotent stem cells can be maintained in culture for 20 or more passages; b) the cultured pluripotent stem cells can attach to and spread faster on the culture substrate, do not differentiate with repeated passaging, contain fewer dying cells, are more motile as cells or colonies, or grow faster, or any combination thereof, as compared to the control pluripotent cells; c) the additive can be sodium acetate; d) or any combination of a)-c).

In another aspect, a method of rescuing a culture of pluripotent stems cells that has begun differentiating is provided. The method includes: a) supplementing a PSC culture medium with an additive that includes a source of acetate ions, a metabolic derivative of acetic acid, a carboxylic acid, or a physiologically acceptable salt of the carboxylic acid, or a combination thereof; and b) incubating the culture of pluripotent stems cells in the supplemented culture medium. In the method, the additive is supplemented in an amount effective to reduce or prevent further differentiation of the culture of pluripotent stems cells as compared to control pluripotent cells cultured in the PSC culture medium not supplemented with the additive. The rescued cells can be passaged in supplemented PSC culture media.

In a further aspect, a method of creating induced pluripotent stems cells is provided. The method includes: a) supplementing a PSC culture medium with an additive that includes a source of acetate ions, a metabolic derivative of acetic acid, a carboxylic acid, or a physiologically acceptable salt of the carboxylic acid, or a combination thereof; and b) culturing reprogramming cells in the supplemented PSC culture medium. In the method, the additive is supplemented in an amount effective to increase production of induced pluripotent stem cells derived from the reprogramming cells as compared to control reprogramming cells cultured in the PSC culture medium not supplemented with the additive. The induced cells can be passaged in supplemented PSC culture media.

In another aspect, a method of improving a PSC culture medium is provided. The method includes supplementing the culture medium with an additive that includes a source of acetate ions, a metabolic derivative of acetic acid, a carboxylic acid, or a physiologically acceptable salt of the carboxylic acid, or a combination thereof. In the method, the additive is supplemented in an amount effective to maintain pluripotency of pluripotent stem cells, reduce or prevent further differentiation of a culture of pluripotent stem cells that has begun differentiating, or increase production of induced pluripotent stem cells from reprogramming cells, as compared to respective control cells cultured in the PSC culture medium not supplemented with the additive. Accordingly, the additive is non-toxic in the amount chosen.

In a further aspect, an improved PSC culture medium is provided. The culture medium includes amino acids, vitamins, minerals, growth factors, albumin, and transferrin, and is supplemented with an additive the includes a source of acetate ions, a metabolic derivative of acetic acid, a carboxylic acid, or a physiologically acceptable salt of the carboxylic acid, or a combination thereof. In the culture medium, the additive is supplemented in an amount effective to maintain pluripotency of pluripotent stem cells, reduce or prevent further differentiation of a culture of pluripotent stem cells that has begun differentiating, or increase production of induced pluripotent stem cells derived from reprogramming cells, as compared to respective control cells cultured in the PSC culture medium not supplemented with the additive.

In any embodiments of the methods of improving the culturing of pluripotent stem cells, rescuing a culture of pluripotent stems cells, creating induced pluripotent stems cells, or improving a PSC culture medium, or embodiments of the improved PSC culture medium, the source of acetate ions can be acetic acid, a physiologically acceptable salt of acetic acid, or a metabolic precursor of acetic acid, or a combination thereof. Also, the carboxylic acid can have the formula RCOOH, wherein R is a saturated or unsaturated hydrocarbyl group, or a saturated or unsaturated substituted hydrocarbyl group.

Further, in any embodiment of the methods and the culture medium: a) in the absence of the additive from the PSC culture medium, the pluripotent stem cells are not maintained in an undifferentiated pluripotent state in culture; b) in the absence of the additive from the PSC culture medium, colonies of the pluripotent stem cells in culture can show radial alignment of cells, spiky edges, or differentiating cells, or any combination thereof; c) the additive can be added to the culture medium in hydrated or anhydrous form, which in particular embodiments is added in hydrated form; d) the amount of the additive, and in particular, acetic acid, or the physiologically acceptable salt of acetic acid, the metabolic precursor of acetic acid, the metabolic derivative of acetic acid, or a combination thereof, or NaOAc, can be from about 1 mM to about 10 mM or more, and more particularly, about 5 mM to about 10 mM or more; e) the pluripotent stem cells can be maintained in an undifferentiated pluripotent state in culture for ≥10, ≥12, ≥20, or ≥25 passages; f) the pluripotent stem cells can be maintained in the additive-supplemented PSC culture medium such that the cells attach to and spread faster on a substrate, do not differentiate with repeated passaging, contain fewer dying cells, are more motile as cells or colonies, or grow faster, or any combination thereof, compared to control stem cells maintained in the PSC culture medium without the additive; g) the pluripotent stem cells can be embryonic stem cells or induced pluripotent stem cells; h) the pluripotent stem cells can be human pluripotent stem cells; i) pluripotent stem cells can begin to differentiate if the additive is removed from the cell culture medium; j) the pluripotent cells can be cultured in a bioreactor, or the PSC culture medium can be added to a bioreactor, which can provide, for example, for large scale growth of pluripotent cells; k) the additive can be an analog of acetic acid; or l) any combination of a)-k).

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
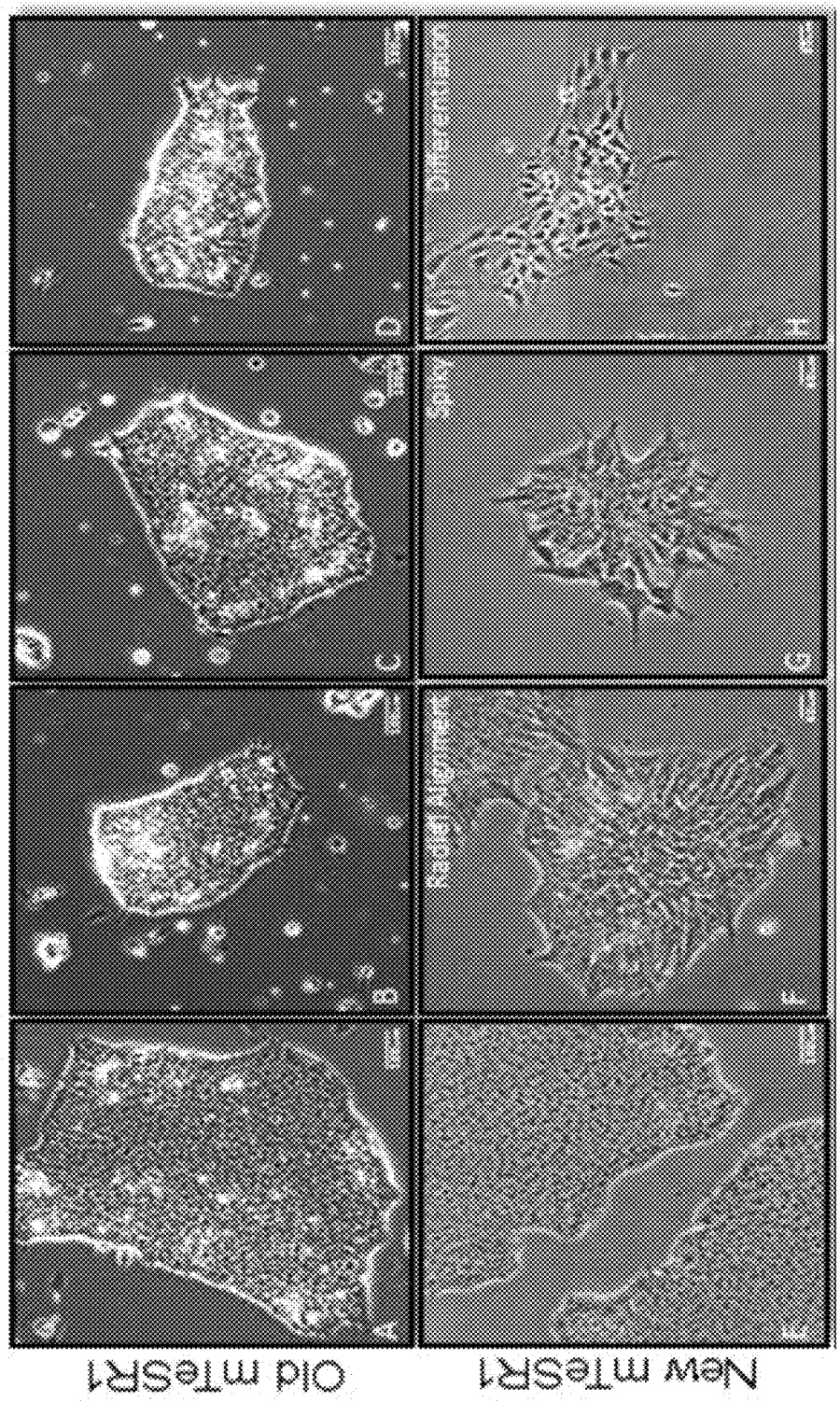
FIG. 1 is a panel showing examples of the problems found with existing hPSC culture media. (1A-1D) hPSC colonies with desirable morphology characteristic of undifferentiated pluripotent cells. Colonies have defined edges, high nuclear to cytoplasmic ratio, and tight cell-to-cell interactions. (1E-1H) Colonies that have not maintained pluripotency and started differentiation. Some colonies in this culture have normal morphology (1E), while many/most show radial alignment of cells on the edges of the colonies (1F), spiky edges (1G), and fully differentiated neurons (1H).

In some embodiments, a PSC culture medium is supplemented with an additive comprising a source of acetate ions, a metabolic derivative of acetic acid, a carboxylic acid, or a physiologically acceptable salt of the carboxylic acid, or a combination thereof. A PSC culture medium supports the maintenance and growth of pluripotent stem cells and typically contains amino acids, vitamins, minerals, growth factors, albumin, and transferrin. A number of PSC culture media have been prepared, and various PSC culture media are commercially available. Examples of PSC culture media and their preparation can be found in Human Stem Cell Manual (Second Edition), A Laboratory Guide, Loring and Peterson, Ed., Elsevier, Inc. 2012, and in a commercial manual on the World Wide Web at cdn.stemcell.com/media/files/manual/MA29106-Maintenance_Human_Pluripotent-_Stem Cells_mTeSR1.pdf?_ga=1.244689923.760597027.1481748091, both incorporated by reference herein.

In some cases, a PSC culture medium may already contain an amount of the additive. For example, the medium may contain sodium acetate. In such cases, by supplementing the medium with an additional amount of the additive, the supplemented PSC culture media can maintain pluripotency of the pluripotent stem cells to a greater extent than the original, non-supplemented PSC culture medium.

The source of acetate ions can be acetic acid, a physiologically acceptable salt of acetic acid, a metabolic precursor of acetic acid, or a combination thereof. Examples of physiologically acceptable salts of acetic acid include, but are not limited to, sodium acetate (NaOAc), sodium diacetate, ammonium acetate, formamidine acetate, and metal salts including, but not limited to, potassium acetate, aluminum acetate, and acetates of the transition metals Mn(II), Co(II), Cu(II), Ni(II), Zn(II), Ag(I), Mo(II), Ce(III), La(III)). Hydrated salts of acetate, such as NaOAc.3H2O, can also be a source of the acetate ion.

The source of acetate ions can be any chemical that gives rise to acetate ions in the cell as a result of cellular metabolism. Examples of such chemicals include, but are not limited to, pyruvate and citrate, and the like.

In some embodiments, the additive can be a metabolic derivative of acetic acid. Examples of such derivatives include, but are not limited to, acetyl coenzyme A (acetyl-CoA), and the like.

In general, various molecules can be metabolized into acetate or produced from acetate by cells. For example, acetyl-CoA can be made from acetate, and should help maintain pluripotency and promote growth. Pyruvate is an example of an upstream metabolite of acetic acid. Pyruvate is metabolized to acetyl-CoA, citrate, and then acetate. The additive is contemplated to be any chemical that is metabolized to acetate or acetyl CoA, or metabolically derived from acetate. For example, this includes molecules that lead to the production of acetate, the conversion of acetate into acetyl-CoA, and the interconversion of acetyl-CoA into glucose, amino acids and fatty acids, and can involve pathways such as the TCA cycle, glycolysis, and alcohol metabolism via alcohol dehydrogenase.

In some embodiments, the additive is a saturated or unsaturated carboxylic acid of the formula RCOOH, where R can be a saturated or unsaturated hydrocarbyl group or a saturated or unsaturated substituted hydrocarbyl group. In some embodiments, R can be a $C_1$-$C_{20}$ or greater hydrocarbyl or substituted hydrocarbyl group, or more particularly a $C_1$-$C_{10}$ hydrocarbyl or substituted hydrocarbyl group. In some embodiments, the additive comprises an anion based on the chemical series RCOO⁻, where R can be a saturated or unsaturated hydrocarbyl group or a saturated or unsaturated substituted hydrocarbyl group. In some embodiments, R is a $C_1$-$C_{20}$ or greater hydrocarbyl or substituted hydrocarbyl group, or more particularly a $C_1$-$C_{10}$ hydrocarbyl or substituted hydrocarbyl group. In some embodiments of RCOOH or RCOO⁻, R can be a $C_1$-$C_5$ alkyl group, or a $C_1$-$C_{10}$ or greater alkyl group.

A hydrocarbyl group refers to any monovalent or divalent linear, branched or cyclic group that contains only carbon and hydrogen atoms. Examples of such groups include, but are not limited to univalent groups such as alkyl, alkenyl, alkynyl, aryl, aralkyl, cycloalkyl, cycloalkenyl or cycloalkynyl, and divalent groups such as alkylene, alkenylene, alkynylene or arylene.

The term "substituted" in reference to a hydrocarbyl group refers to a hydrocarbyl group in which one or more bonds to a hydrogen atom contained within the group is replaced by a bond to a non-hydrogen atom of a substituent group. Examples of non-hydrogen atoms include, but are not limited to, carbon, oxygen, nitrogen, phosphorus, sulfur, selenium, arsenic, chlorine, bromine, silicone and fluoride. Examples of substituent groups include, but are not limited to, halo, perhaloalkyl such as trifluoromethyl, hydroxyl, amino, alkoxy, aryloxy, carboxy, mercapto, cyano, nitro, ester, ether, thioether, trialkylsilyl, amide and hydrocarbyl groups.

Physiologically acceptable salts are well known in the art and include salts prepared from physiologically acceptable non-toxic acids and bases, including inorganic and organic acids/bases. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, hydrochloric, hydrobromic, phosphoric, sulfuric acids, and the like. Salts formed with, for example, a free carboxy group, can be derived from inorganic bases including, but not limited to, sodium, potassium, ammonium, or calcium hydroxides, and organic bases including, but not limited to, isopropylamine, trimethylamine, histidine, and procaine. Physiologically acceptable hydrated salts of carboxylic acids can also be a source of the RCOO⁻ ion.

The additive can comprise any combination of a source of acetate ions, a metabolic derivative of acetic acid, a carboxylic acid, and a physiologically acceptable salt of the carboxylic acid. Further, the additive can comprise more than one source of acetate ions, more than one metabolic derivative of acetic acid, more than one carboxylic acid, or more than one physiologically acceptable salt of the carboxylic acid, or any combination thereof.

Pluripotency can be assessed in a pluripotent stem cell culture, for example, by testing for the presence of pluripotency markers such as NANOG, OCT4, SOX2, or SSEA3.

Differentiation of pluripotent stem cells can be assessed by the presence of one or more early differentiation markers such as SOX17, Brachyury, or PAX6 for the three germ layer lineages, endodermal, mesodermal, and ectodermal respectively.

Induced pluripotent stem cells can be prepared by methods well known in the art. For example, the induced pluripotent stem cells can be prepared using a variety of integrative and non-integrative reprogramming systems that involve reprogramming of somatic cells by expressing pluripotency-related transcription factors OCT4, SOX2, KLF4 and c-MYC (see Gonzalez, F. et al, Methods for making induced pluripotent stem cells: reprogramming à la carte; Nature Reviews Genetics 12, 231-242 (2011), incorporated by reference herein in its entirety).

The present invention may be better understood by referring to the accompanying examples, which are intended for illustration purposes only and should not in any sense be construed as limiting the scope of the invention.

Example 1

Standard hPSC culture medium (e.g. mTeSR manufactured by Stem Cell Technologies, Vancouver, Canada) can be greatly improved by the addition of 5 mM-10 mM sodium acetate trihydrate (NaOAc.3H2O) before placing medium on cells. FIG. 1 shows human embryonic stem cell colonies growing in an old batch of mTeSR culture medium that maintained pluripotency vs a new batch that does not support pluripotency. Colonies in the old batch have cells that are tightly packed and the edges of the colonies are smooth, not pointy (FIGS. 1A-D). These are hallmarks of healthy pluripotent human embryonic stem cells (hESC) in culture. In new batches of mTeSR, the edges of colonies show radial alignment of cells (FIG. 1E, F), spikey edges (FIG. 1G), and differentiation (FIG. 1H). These are not normal pluripotent stem cell morphologies and are observed when colonies begin to differentiate.

Figure 2:
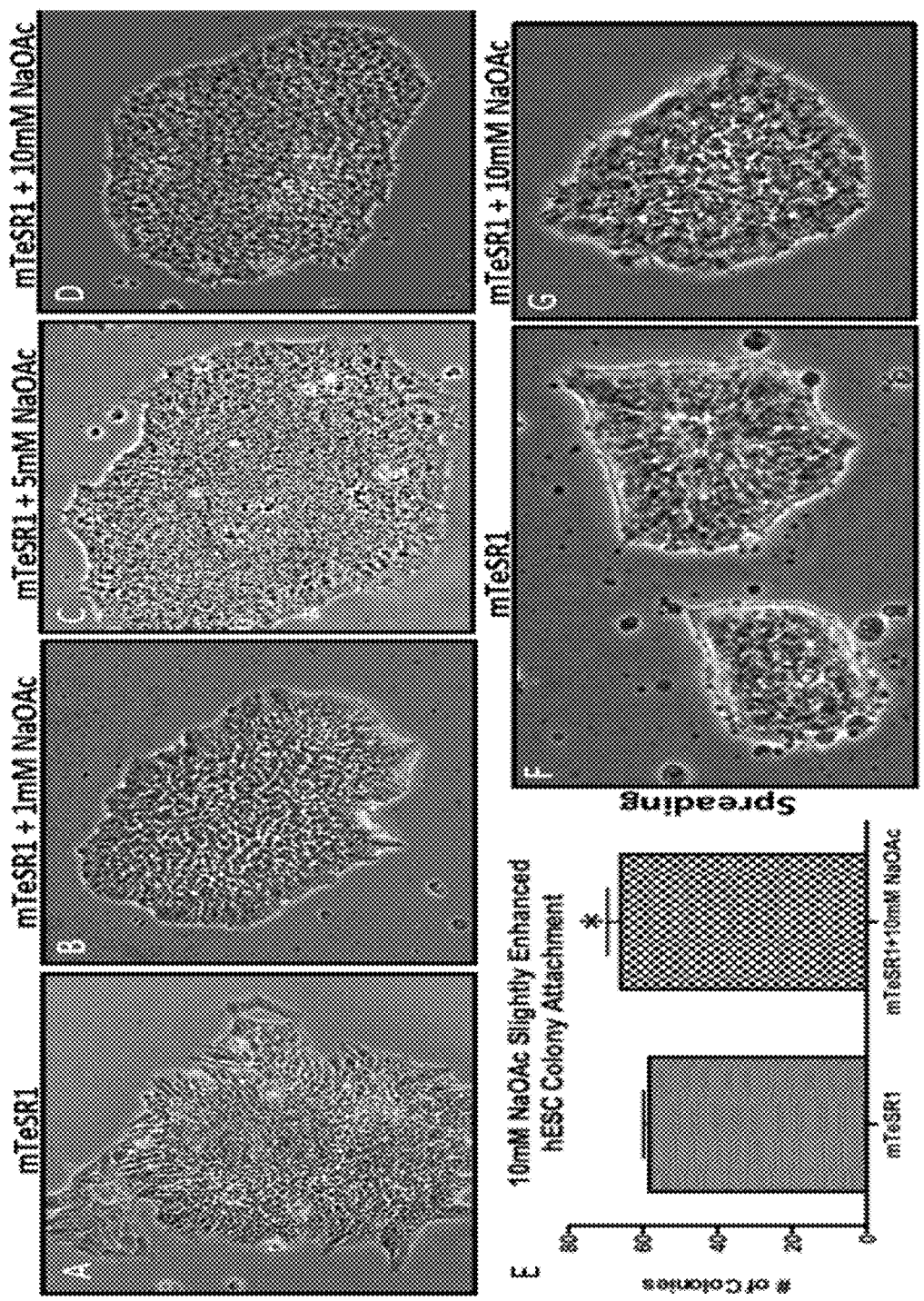
FIG. 2 is a panel showing that the addition of NaOc.3H2O to hPSC culture medium rescued human embryonic stem cell cultures, improved attachment/spreading, and decreased cell death. (2A) Colony grown in mTeSR1 shows abnormal morphology associated with imminent differentiation, (2B) Colony incubated in mTeSR1+1 mM NaOAc.3H2O shows improved morphology, (2C) Colony incubated in mTeSR1+5 mM NaOAc.3H2O shows even more improvement of morphology, (2D) Colony incubated mTeSR1+10 mM NaOAc.3H2O shows normal morphology characteristic of pluripotent cells. (2E) Comparison of hESC attachment in mTeSR1 or mTeSR1+10 mM NaOAc.3H2O, (2F) Spreading of colonies in mTeSR1 only is poor; colonies are elevated, not flat, (2G) Spreading of colonies in mTeSR1+10 mM NaOAc.3H2O is improved; colonies are flatter and spread faster. (2H-2M) StemCellQC™ time-lapse video bioinformatics analysis of colonies grown in mTeSR1 only or mTeSR1+10 mM NaOAc. Colonies cultured in mTeSR1+10 mM NaOAc grow faster (2H and 2I), are rounder (normal morphology) (2J), have better motility (2K and 2L), and have fewer dead cells (2M).
Figure 2:
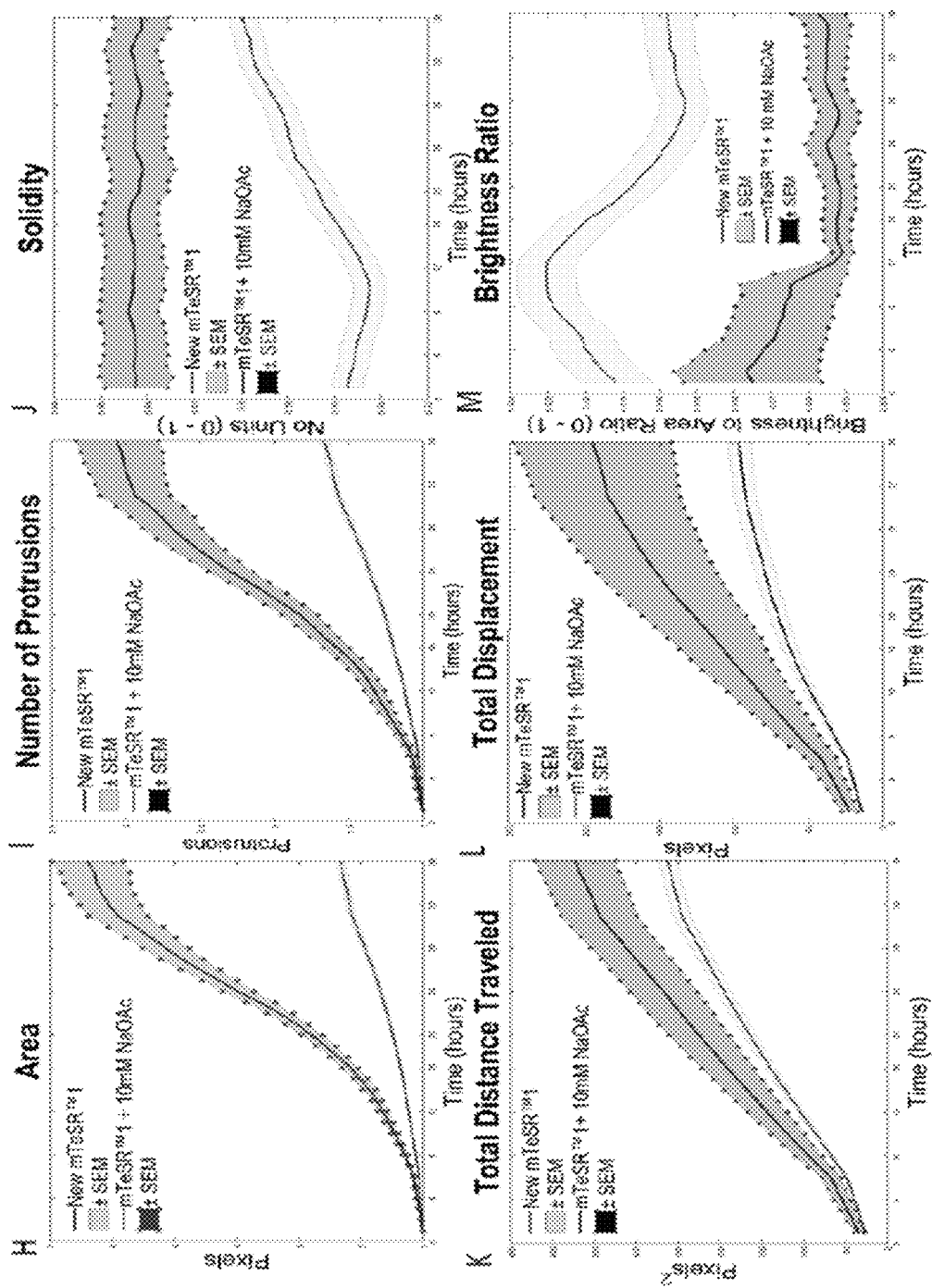

Addition of 5 mM-10 mM of the additive NaOAc.3H2O to mTeSR allowed colonies to maintain the normal round, tightly packed morphology of pluripotent hESC (FIG. 2A-D). This effect was dose dependent. In new mTeSR without the additive, hESC showed pointy edges and differentiation at the edge of colonies (FIG. 2A). Addition of 1 mM NaOAc.3H2O to mTeSR had little effect on colony morphology; cells were loosely packed, edges were pointy and differentiation occurred (FIG. 2B). In mTeSR with 5 or 10 mM NaOAc.3H2O, colony morphology was restored to normal for cells that are pluripotent (FIG. 2D). In 10 mM NaOAc.3H2O, cells in the colony were tightly packed and edges were smooth, not pointy. Colonies did not differentiate even when passaged in mTeSR with the NaOAc.3H2O supplement over 20 times Addition of the additive NaOAc.3H2O to mTeSR also enhanced the attachment of cells to their substrate (FIG. 2E). While the difference in attachment between mTeSR and mTeSR plus the additive was modest, it was significantly different. In the additive-supplemented medium, the hESC colonies also spread faster on the substrate (FIGS. 2F and G). This is very important and may be a factor in preventing unwanted differentiation. FIGS. 2H-M show video bioinformatics analysis of live hESC growing in vitro. This analysis was done on time-lapse images of living cultures and allows quantitative comparison between cells grown in different media. These data clearly show the following: (1) Growth rate was much faster in mTeSR containing the additive (FIG. 2H); (2) Solidity was closer to 1 in colonies cultured in the media indicating that they had a rounder morphology; colonies in just mTeSR sometimes were abnormally distorted or curved, which is shown by their lower solidity (FIG. 2J); (3) Motility was greater for colonies in mTeSR with the additive (FIGS. 2 J-K); this is important as motile colonies/cells are better able to spread rapidly and find other cells/colonies that they can merge with. Rapid formation of colonies following plating is important for cell survival; and (4) Fewer cells died in medium containing the additive (FIG. 2 L). The brightness to area ratio is a measurement of cell death; the low brightness to area ratio of the colonies grown in mTeSR plus the additive demonstrates that little cell death occurred, while colonies in mTeSR alone extruded numerous dying cells, as shown by the high brightness to area ratio (FIG. 2M).

Figure 3:
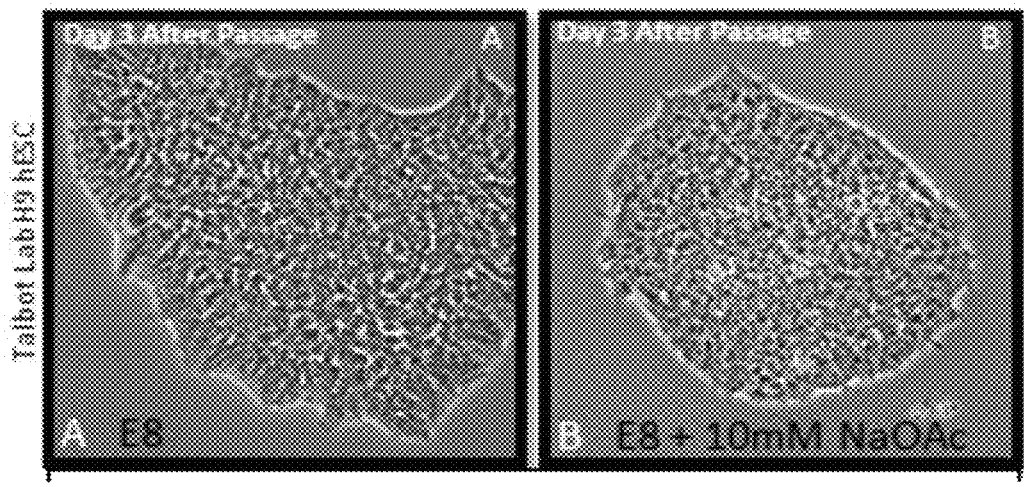
FIG. 3 is a panel showing that the addition of NaOAc.3H2O improves colony morphology and health in other commercially available media (e.g. Essential-8). (3A) Colony cultured in Essential-8, purchased from Stem Cell Technologies, (3B) Colony cultured in Essential-8+10 mM NaOAc.3H2O showing improved morphology.

The additive worked with other culture media. FIG. 3 shows colonies cultured in Essential-8 medium alone (A) and in Essential-8 plus the additive (B). The colony in Essential-8 alone has radially aligned cells at its edges. The colony in Essential-8 plus the additive looks normal. It is round with a smooth edge and tightly packed cells, characteristics of pluripotent colonies.

Figure 4:
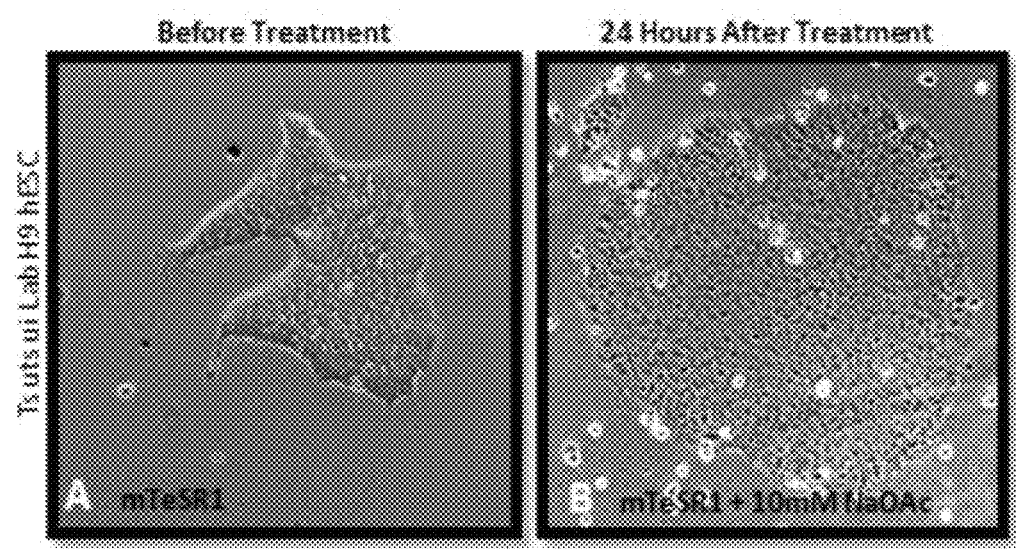
FIG. 4 is a panel showing that cells obtained from another lab recover normal morphology when incubated in mTeSR supplemented with NaOAc.3H2O. (4A) Colony obtained from Dr. Hideaki Tsutsui's lab at the University of California, Riverside, Calif., USA, cultured in mTeSR1. (4B) Colony from Dr. Tsutsui's lab after 24 hours of culture in mTeSR containing 10 mM NaOAc.3H2O.

The additive also worked with H9 hESC obtained from other labs. The colony in FIG. 4A is an H9 colony obtained from another investigator's lab. It has an irregular shape, and it has not spread well on the substrate. The colony in FIG. 4B is an H9 colony from the same plate after it was placed in mTeSR plus the additive. The colony has spread on the substrate and has a round morphology with smooth edges, characteristic of pluripotent cells. The cells in the middle of the colony also appear to be more tightly packed in mTeSR1+10 mM NaOAc.3H2O than in mTeSR1 alone.

Figure 5:
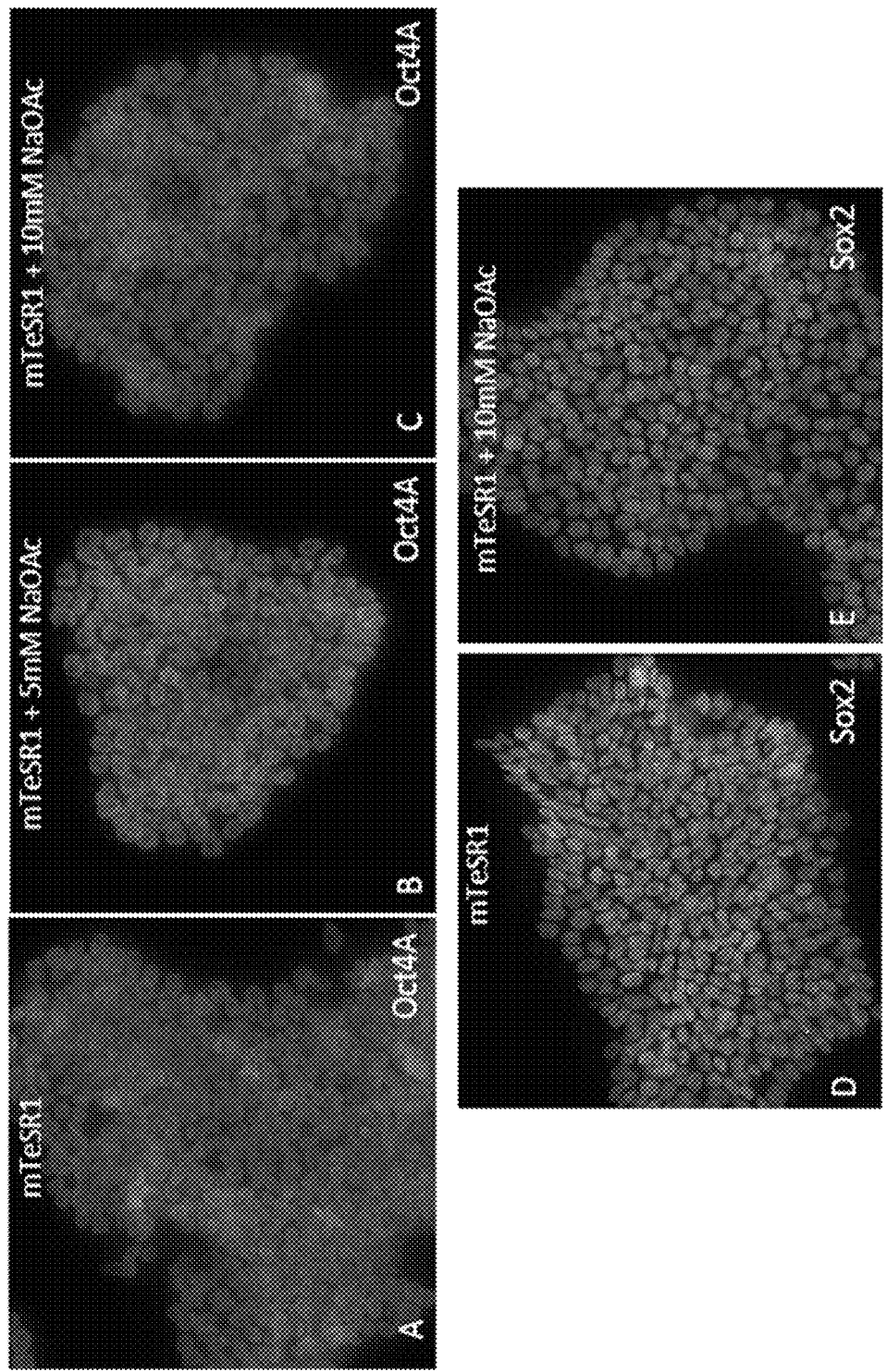
FIG. 5 is a panel showing the verification of pluripotency using Oct4A and SOX2 markers. hESC colonies were cultured in mTeSR1 or mTeSR1+5 or 10 mM NaOAc. Positive Oct4A staining was observed in (5A) mTeSR1, (5B) mTeSR1+5 mM NaOAc, and (5C) mTeSR1+10 mM NaOAc. Positive Sox2 staining was observed in (5D) mTeSR1, (5E) mTeSR1+10 mM NaOAc.
Figure 6:
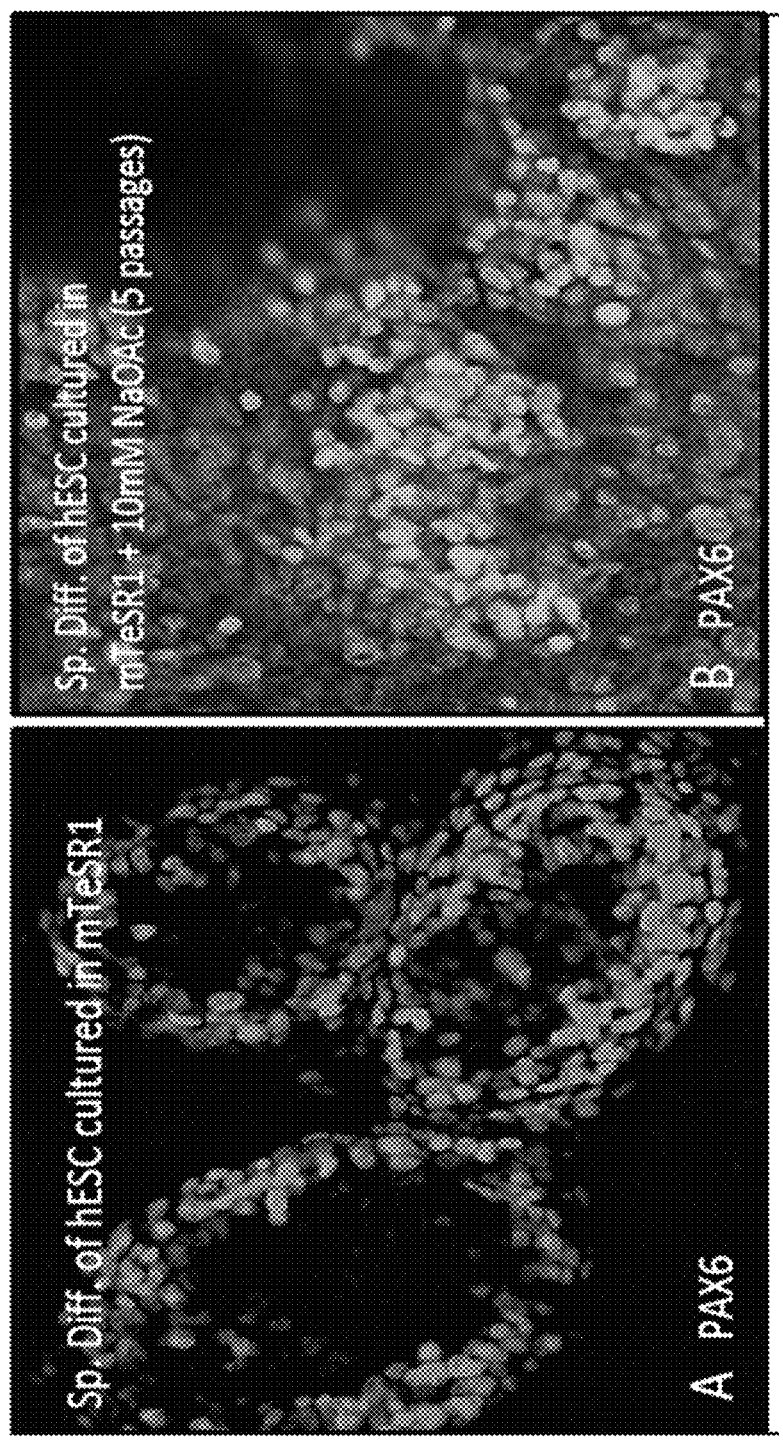
FIG. 6 is a panel showing that colonies incubated in medium containing NaOAc.3H2O can differentiate when transferred to differentiation medium. (6A) Spontaneous differentiation of hESC incubated in mTeSR only then transferred to differentiation medium. Cells stain positively for Pax6, an ectodermal marker. (6B) hESC incubated in mTeSR plus NaOAc.3H2O, then transferred to differentiation medium. Cells stained positively for Pax6 indicating they differentiated into ectoderm.

Molecular biomarkers for pluripotency were maintained in mTeSR containing the additive (FIG. 5). Colonies were incubated in mTeSR or mTeSR plus varying concentrations of NaOAc.3H2O. As shown in FIG. 5, colonies in mTeSR plus the additive showed bright labeling of Oct 4 (a biomarker for pluripotency). Fluorescence was strongest at the 10 µM concentration.

hESC colonies grown in mTeSR plus the additive were able to differentiate when transferred to a differentiation medium. FIG. 6 shows colonies allowed to spontaneously differentiate in vitro. These colonies were labeled with an antibody to Pax6, a marker for ectodermal differentiation. As seen in the micrographs, cells cultured in mTeSR plus the additive labeled strongly for Pax6 indicating they had entered the ectodermal lineage. The additive thus does not prevent differentiation of hESC once they are transferred to differentiation media One way to practice embodiments of the invention is to add the NOAc.3H2O additive, for example, to PSC culture medium before placing the medium on cells. Cells will respond well when cultured in the medium. The ability of the additive to function effectively is dose dependent. If a culture has begun differentiating, the additive can be added at 10 mM and it will rescue the culture and prevent further differentiation. For routine maintenance of pluripotency in healthy colonies, 5 mM of NaOAc can be used. Other concentrations may be optimal for other cells lines or other culture media.

The chemical additive could be added to any culture medium intended for use with pluripotent stem cells. Other species of the chemical (metabolites, derivatives, isoforms etc.) could be used and may work as well or better. The chemical could be used with cells grown on different substrates. Matrigel and Geltrex have been tried, but it may also work well with cells on vitronectin or other platforms. The chemical additive could also be added to media for the culture of other pluripotent cell lines. The H9 line that reported on here is the "gold standard" in hESC research. It is the most widely used line in pluripotent stem cells laboratories, and it is important that it can be grown properly in culture. However other hESC lines are also in use and could benefit by addition of NaOAc.3H2O to culture media.

As stated above, cell quality and maintenance of pluripotency are currently problems in labs working with hPSC. Cell quality is improved in the culture medium with addition of NaOAc.3H2O and pluripotency is maintained during repeated passaging. The supplemented medium specifically improves pluripotent cell culture in the following five ways: (1) cells attach to and spread faster on the substrate (faster spreading is correlated with healthy colonies that do not differentiate); (2) cells do not differentiate even with repeated passaging; (3) fewer cells die in the medium; (4) cells/colonies are more motile in the medium; and (5) cells grow faster in the medium, which facilitates expansion and is resource and time saving. These are major advantages over the commercial medium (mTeSR) which is most widely used in PSC labs. Maintaining pluripotency, growth, motility, and overall colony health in a xeno-free and serum-free environment is essential for basic, translational, and clinical work with pluripotent stem cells. Thus, this discovery is an important breakthrough in improving PSC culture.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method for improving the culturing of pluripotent stem cells in a pluripotent stem cell (PSC) culture medium, comprising supplementing the PSC culture medium with 5 mM to 10 mM sodium acetate and culturing the pluripotent stem cells in the supplemented PSC culture medium; wherein the additive is effective to maintain pluripotency of the pluripotent stem cells to a greater extent as compared to control pluripotent cells cultured in the PSC culture medium not supplemented with the additive.

2. The method of claim 1, wherein the pluripotency of the pluripotent stem cells is maintained in culture for 20 or more passages.

3. The method of claim 1, wherein the cultured pluripotent stem cells attach to and spread faster on culture substrate, do not differentiate with repeated passaging, contain fewer dying cells, are more motile as cells or colonies, or grow faster, or any combination thereof, as compared to the control pluripotent cells.

4. A method of rescuing a culture of pluripotent stems cells that has begun differentiating, comprising supplementing a PSC culture medium with 10 mM sodium acetate and incubating the culture of pluripotent stems cells in the supplemented culture medium; wherein the additive is effective to reduce or prevent further differentiation of the culture of pluripotent stems cells as compared to control pluripotent cells cultured in the PSC culture medium not supplemented with the additive.

5. A method of creating induced pluripotent stems cells, comprising supplementing a PSC culture medium with 5 mM to 10 mM sodium acetate and culturing reprogramming cells in the supplemented PSC culture medium; wherein the additive is effective to increase production of induced pluripotent stem cells derived from the reprogramming cells as compared to control reprogramming cells cultured in the PSC culture medium not supplemented with the additive, the source of acetate ions comprising acetic acid, a physiologically acceptable salt of acetic acid, or a metabolic precursor of acetic acid, or a combination thereof.

6. A method of improving a PSC culture medium, comprising supplementing the culture medium with 5 mM to 10 mM sodium acetate wherein the additive is effective to maintain pluripotency of pluripotent stem cells, reduce or prevent further differentiation of a culture of pluripotent stem cells that has begun differentiating, or increase induction of pluripotent stem cells from reprogramming cells, as compared to respective control cells cultured in the PSC culture medium not supplemented with the additive.

* * * * *